US008391942B2

(12) United States Patent
Benni (10) Patent No.: US 8,391,942 B2
(45) Date of Patent: Mar. 5, 2013

(54) METHOD AND APPARATUS FOR DETERMINING CEREBRAL DESATURATION IN PATIENTS UNDERGOING DEEP HYPOTHERMIC CIRCULATORY ARREST

(75) Inventor: Paul Benni, Guilford, CT (US)

(73) Assignee: CAS Medical Systems, Inc., Branford, CT (US)

( * ) Notice: Subject to any disclaimer, the term of this patent is extended or adjusted under 35 U.S.C. 154(b) by 671 days.

(21) Appl. No.: 12/574,412

(22) Filed: Oct. 6, 2009

(65) Prior Publication Data

US 2010/0087719 A1  Apr. 8, 2010

Related U.S. Application Data

(60) Provisional application No. 61/103,035, filed on Oct. 6, 2008, provisional application No. 61/103,058, filed on Oct. 6, 2008.

(51) Int. Cl.
*A61B 5/00* (2006.01)

(52) U.S. Cl. ...................................................... 600/323

(58) Field of Classification Search ................... 600/323
See application file for complete search history.

(56) References Cited

U.S. PATENT DOCUMENTS

| | | | |
|---|---|---|---|
| 3,638,640 A | 2/1972 | Shaw | |
| 4,281,645 A | 8/1981 | Jobsis | |
| 4,570,638 A | 2/1986 | Stoddart et al. | |
| 4,725,147 A | 2/1988 | Stoddart | |
| 4,768,516 A | 9/1988 | Stoddart et al. | |
| 4,805,623 A | 2/1989 | Jobsis | |
| 4,817,623 A | 4/1989 | Stoddart et al. | |
| 4,907,876 A | 3/1990 | Suzuki et al. | |
| 5,054,488 A | 10/1991 | Muz | |
| 5,139,025 A | 8/1992 | Lewis et al. | |
| 5,153,669 A | 10/1992 | DeGroot | |
| 5,213,099 A * | 5/1993 | Tripp, Jr. | 600/324 |
| 5,251,632 A | 10/1993 | Delpy | |
| 5,337,743 A * | 8/1994 | Repperger et al. | 600/323 |
| 5,349,961 A | 9/1994 | Stoddart et al. | |
| 5,482,034 A | 1/1996 | Lewis et al. | |
| 5,517,987 A | 5/1996 | Tsuchiya | |
| 5,529,065 A | 6/1996 | Tsuchiya | |
| 5,632,273 A | 5/1997 | Suzuki | |
| 5,676,142 A | 10/1997 | Miwa et al. | |
| 5,770,454 A | 6/1998 | Essenpreis et al. | |
| 5,772,589 A | 6/1998 | Bernreuter | |
| 5,803,909 A | 9/1998 | Maki et al. | |
| 5,853,370 A | 12/1998 | Chance et al. | |
| 5,902,235 A | 5/1999 | Lewis et al. | |
| 6,192,260 B1 | 2/2001 | Chance | |
| 6,456,862 B2 | 9/2002 | Benni | |
| 6,615,065 B1 | 9/2003 | Barrett et al. | |
| 7,072,701 B2 | 7/2006 | Chen et al. | |

(Continued)

OTHER PUBLICATIONS

Benni et al. "A Novel Near-Infrared Spectroscopy (NIRS) System for Measuring Regional Oxygen Saturation", Department of Anesthesia, Robert Wood Johnson Medical School, May 22, 1995.

(Continued)

*Primary Examiner* — Clayton E. Laballe
*Assistant Examiner* — Leon W Rhodes, Jr.
(74) *Attorney, Agent, or Firm* — O'Shea Getz P.C.

(57) ABSTRACT

A method and apparatus for determining cerebral oxygen saturation in a subject is provided. The method comprises the steps of: a) determining tissue oxygen saturation values using a NIRS type oximeter over a period of time; b) modeling a rate of change in the tissue oxygen saturation values; and c) determining an amount of time until a predetermined tissue oxygen saturation value is reached using the modeling of the tissue oxygen saturation values.

4 Claims, 5 Drawing Sheets

U.S. PATENT DOCUMENTS

| | | | | |
|---|---|---|---|---|
| 8,064,975 | B2* | 11/2011 | Pav | 600/323 |
| 2007/0203406 | A1* | 8/2007 | Anderson et al. | 600/323 |
| 2008/0183058 | A1* | 7/2008 | Mannheimer | 600/323 |

OTHER PUBLICATIONS

Jacques et al. "The Melanosome: Threshold Temperature for Explosive Vaporization and Internal Absorption Coefficient During Pulsed Laser Irradiation", Photochemistry and Photobiology, vol. 53, No. 6, pp. 769-775, 1991.

Griepp et al. "Prosthetic Replacement of the Aortic Arch", J Thorac Cardiovasc Surg 1975, 70, 1051-1063.

Ergin et al. "Experience with Profound Hypothermia and Circulatory Arrest in the Treatment of Aneurysms of the Aortic Arch: Aortic Arch Replacement for Acute Arch Dissections", J Thorac Cardiovasc Surg 1982, 649-655.

Gega et al. "Straight Deep Hypothermic Arrest: Experience in 394 Patients Supports its Effectiveness as a Sole Means of Brain Preservation", Ann Thorac Surg. Sep. 2007, 84(3), 759-766.

Riech et al. "Neuropsychologic Outcome After Deep Hypothermic Circulatory Arrest in Adults", J Thorac Cardiovasc Surg. Jan. 1999 117(1), 156-163.

Leggat et al. "Early Detection of an Acute Cerebral Event During Cardio-Pulmonary Bypass Utilizing a Bispectral Index Monitor", Semin Cardiothorac Vasc Anesth. 12, 82-82, 2008.

Reich et al. "Using Jugular Bulb Oxyhemoglobin Saturation to Guide Onset of Deep Hypothermic Circulatory Arrest Does Not Affect Post-Operative Neuropsychological Function", Eur J Cardiothorac Surg. Mar. 2004, 12(1), 401-406.

Fischer SW. "Recent Advances in Application of Cerebral Oximetry in Adult Cardiovascular Surgery", Semin Cardiothorac Vasc Anesth. Mar. 2008, 12(1), 60-69.

Ito et al. "Arterial Fraction of Cerebral Blood Volume in Humans Measured by Positron Emission Tomography", Ann Nucl Med. Apr. 2001, 15(2), 111-116.

Ito et al. "Human Cerebral Circulation: Positron Emission Tomography Studies", Ann Nucl Med. Apr. 2005, 19(2), 65-74.

Benni et al. "Validation of the CAS Neonatal NIRS System by Monitoring VV-ECMO Patients: Preliminary Results", Adv Exp Med Biol. 2005, 566, 195-201.

Elwell CE. "A Practical Users Guide to Near Infrared Spectroscopy", Hamamatsu Phototonics KK, 1995.

Matcher et al. "Performance Comparison of Several Published Tissue Near-Infrared Spectroscopy Algorithms", Anal Biochem, May 1995, 227(1), 54-68.

Wray et al "Characterisation of the Near Infrared Absorption Spectra of Cytochrome aa3 and Haemoglobin for the Non Invasive Monitoring of Cerebral Oxygenation", Biochem Biophys Acta 1988, 933, 184-192.

Wyatt et al. "Quantification of Cerebral Oxygenation and Haemodynamics in Sick Newborn Infants by Near Infrared Spectrophotometry", Lancet, Nov. 8, 1986, 2(8515), 1063-1066.

Cope et al. "A System for the Long Term MEasurement of Cerebral Blood and Tissue Oxygenation in Newborn Infants by Near Infrared Transillumination", Med Biol Eng Comput, 1988, 26, 289-294.

Wyatt et al. "Quantification of Cerebral Blood Volume in Human Infants by Near-Infrared Spectroscopy", J Apply Physiol. Mar. 1990, 68(3), 1086-1091.

Leung et al. "A New Methd for the Measurement of Cerebral Blood Volume and Total Circulating Blood Volume Using Near Infrared Spatially Resolved Spectroscopy and Indocyanine Green: Application and Validation in Neonates." Pediatr Res. Jan. 2004, 55(1), 134-141.

Schell et al. "Cerebral Monitoring: Jugular Venous Oximetry", Anesth Analg., Mar. 2000, 90(3), 559-566.

Shaaban et al. "Jugular Bulb Oximetry During Cardiac Surgery", Anaesthesia, Jan. 2001, 56(1), 24-37.

Chieregato et al. "Normal Jugular Bulb Oxygen Saturation", J Neuro Neurosurg Psychiatry, 2003, 74, 784-786.

Croughwell et al. "Jugular Bulb Saturation and Cognitive Dysfunction After Cardiopulmonary Bypass", Annals of Thoracic Surger, 1994, 58, 1702-1708.

Macmillan et al. "Cerebrovenous Oxygen Saturation Monitoring: Practical Considerations and Clinical Relevance", Intensive Care Med. 2000, 26, 1028-1036.

MacLeod et al. "Validation of the CAS Adult Cerebral Oximeter During Hypoxia in Healthy Volunteers", Anesth Analg 2006, 102, S162.

MacLeod et al. "Using the CAS Cerebral Oximeter to Estimate Cerebral Venous Oxygen Saturation", presented as the ASA, 2005.

Ferrari et al. "Principles, techniques, and limitations of near infrared spectroscopy", Can J Appl Physiol Aug. 2004;29 (4):463-87.

* cited by examiner

METHOD AND APPARATUS FOR DETERMINING CEREBRAL DESATURATION IN PATIENTS UNDERGOING DEEP HYPOTHERMIC CIRCULATORY ARREST

This application claims the benefit of U.S. Provisional Patent Application Ser. No. 61/103,035, filed Oct. 6, 2008 and U.S. Provisional Patent Application Ser. No. 61/103,058 filed Oct. 6, 2008, both of which are hereby incorporated in their entirety.

This invention was made with Government support under Contract No. 2R44NS045488-02 awarded by the Department of Health & Human Services. The Government has certain rights in the invention.

BACKGROUND OF THE INVENTION

1. Technical Field

The present invention relates to methods and apparatus for determining cerebral oxygenation in general, and to those operable to determine the rate of oxygen desaturation in particular.

2. Background Information

Surgical procedures that involve circulatory arrest can include a risk of neurological sequelae, including those associated with cerebral ischemia. To decrease that risk, it is known to use deep hypothermic circulatory arrest (DHCA) to decrease metabolic demand during the circulatory arrest. Electroencephalographic monitoring (EEG), serial measurements of jugular bulb saturations (jvSO2) and cerebral oximetry based on near infrared spectroscopy can be used to identify cerebral ischemia. In the context of DHCA, however, only cerebral oximetry can be utilized to monitor a patient to detect ischemia during the arrest period itself. This is because isoelectricity caused by deep hypothermia makes EEG monitoring useless, and the circulatory arrest makes jvSO2 measurements unreliable. Consequently, cerebral oximetry currently provides the only technology that can be employed in the DHCA setting.

Current cerebral oximetry devices can provide real-time oxygen saturation information. They do not, however, possess the capability to predict the onset of cerebral ischemia.

SUMMARY OF THE INVENTION

According to an aspect of the present invention, a spectrophotometric examination device is provided that includes at least one sensor and a processor. The at least one sensor has a light signal transmitter operable to transmit at least one light signal, and at least one light signal detector operable to detect the light signal. The sensor is operable to produce at least one sensed signal corresponding to the detected light signal. The processor is adapted to determine an oxygen saturation level in a subject's tissue at a current point in time using the sensed signal. The processor is further adapted to model a rate of change in oxygen saturation level within the subject's tissue, and determine an amount of time between the current point of time and a future point of time when the oxygen saturation level will reach a predetermined value.

According to another aspect of the present invention, a method for determining cerebral oxygen saturation in a subject is provided. The method comprises the steps of: a) determining tissue oxygen saturation values using a NIRS type oximeter over a period of time; b) modeling a rate of change in the tissue oxygen saturation values; and c) determining an amount of time until a predetermined tissue oxygen saturation value is reached using the modeling of the tissue oxygen saturation values.

The foregoing features and advantages of the present invention will become more apparent in light of the following detailed description of exemplary embodiments thereof.

DISCLOSURE OF THE INVENTION

Figure 1:
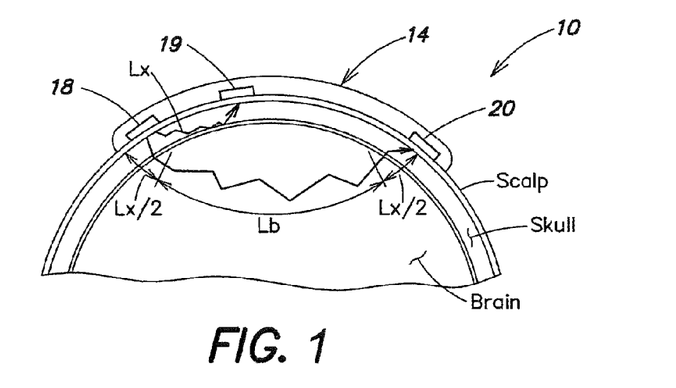
FIG. 1 is a diagrammatic illustration of a NIRS sensor on a subject's head.
Figure 2:
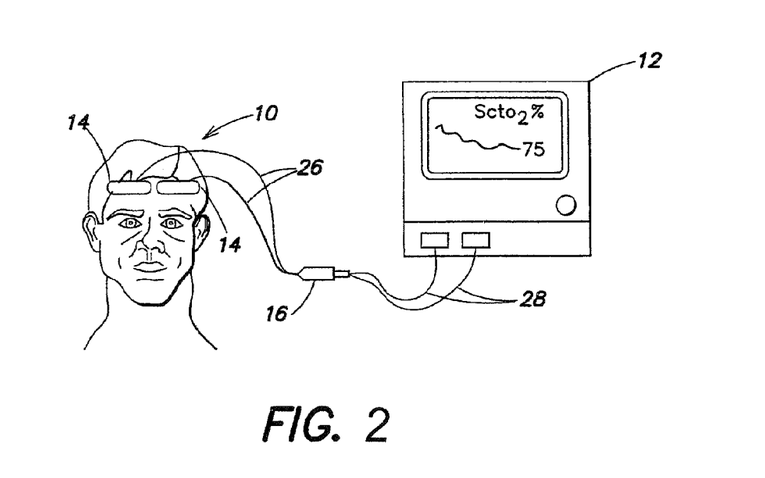
FIG. 2 is a diagrammatic illustration of a NIRS system, including NIRS sensors and a NIRS processing unit.
Figure 3:
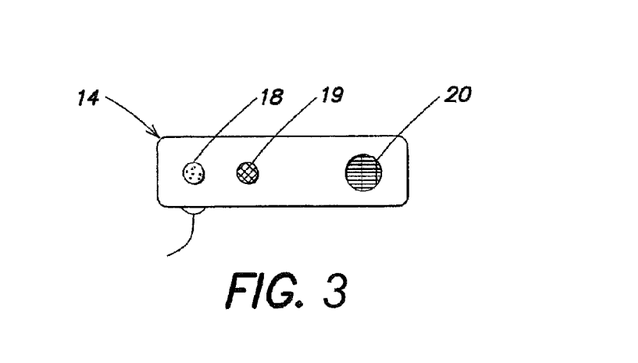
FIG. 3 is a diagrammatic illustration of a NIRS sensor.

Referring to FIGS. 1-3, a method and apparatus for non-invasively determining the blood oxygen saturation level within a subject's tissue is provided that utilizes a near infrared spectrophotometric (NIRS) oximeter that includes at least one sensor 10 capable of transmitting a light signal into the tissue of a subject and sensing the light signal once it has passed through the tissue via transmittance or reflectance, and a processor unit 12 for processing signals representative of the sensed light.

The sensor 10 includes an assembly housing 14 and a connector housing 16. The assembly housing 14, which is a flexible structure that can be attached directly to a subject's body, includes one or more light sources 18 and light detectors 19, 20. A disposable adhesive envelope or pad is preferably used for mounting the assembly housing 14 easily and securely to the subject's skin. Light signals of known but different wavelengths from the light sources emit through a prism assembly. The light sources 18 are preferably laser diodes that emit light at a narrow spectral bandwidth at predetermined wavelengths. The laser diodes may be mounted remotely from the assembly housing 14; e.g., in the connector housing 16 or within the processor unit 12. In these embodiments, a fiber optic light guide is optically interfaced with the laser diodes and the prism assembly that is disposed within the assembly housing 14. In other embodiments, the light sources 18 are mounted within the assembly housing 14. A first connector cable 26 connects the assembly housing 14 to the connector housing 16 and a second connector cable 28 connects the connector housing 16 to the processor unit 12. The light detectors 19, 20 each include one or more photodiodes. The photodiodes are also operably connected to the processor unit 12 via the first and second connector cables 26, 28. The above-described sensor 10 is an example of an acceptable NIRS sensor, and the present invention is not limited to the described embodiment. Other examples of acceptable NIRS sensors are described in U.S. patent application Ser. No. 60/751,009 filed on Dec. 16, 2005, and U.S. patent application Ser. No. 60/729,339 filed on Oct. 21, 2005, both of which applications are commonly assigned to the assignee of the present application and both of which are hereby incorporated by reference in their entirety.

The processor unit 12 includes a processor adapted (e.g., by algorithm in the form of programming, hardware, or some combination thereof) for processing light intensity signals associated with the light sources 18 and the light detectors 19, 20, and processing those signals to determine information including, but not limited to, concentrations of oxy-hemoglobin ($HbO_2$) and deoxy-hemoglobin (Hb) within the subject's tissue, and the tissue oxygen saturation level. In a cerebral oximetry application, the cerebral tissue oxygen saturation of the tissue being interrogated is typically denoted "$SctO_2$". A person of skill in the art will recognize that the processor may assume various forms (e.g., digital signal processor, analog device, etc.) capable of performing the functions described herein. The NIRS processors and algorithms described in U.S. Pat. Nos. 6,456,862; 7,072,701; and application Ser. No. 11/914,074, all of which are hereby incorporated by reference in their entirety, are examples of processors/algorithms that can be used with the present invention to determine the aforesaid oximetry information. The FORE-SIGHT® cerebral oximeter produced by CAS Medical Systems, Inc. of Branford, Conn., USA is an example of such a NIRS cerebral oximeter which is currently available to the public.

In addition to being adapted to determine the oxygen saturation level within the tissue (e.g., cerebral) being interrogated, in the present invention the processor is further adapted to create one or more models representing the rate of change of the oxygen saturation of the tissue being interrogated; e.g., the rate of oxygen desaturation within the tissue.

The models are created from $SctO_2$ values determined from signal data collected from the subject using the NIRS sensor(s) 10 and processing unit 12 over a period of time. The $SctO_2$ values are analyzed and are form fitted to create a model representative of the values. Acceptable techniques that can be used to fit the values to a particular form include non-linear regression techniques that produce a line having a slope, which line is representative of the calculated $SctO_2$ values. The model may be a linear model (i.e., a single component model) or it may be a multi-component model that has different characteristics in different portions. For example, a first portion of the model may be represented by a first line having a slope that indicates the rate of change of saturation is greater than in a second portion where the slope is relatively speaking more gradual, and therefore indicative of a lesser rate of change of saturation.

Each model can be created in the form of an equation, or a look-up table, or a graphical solution, or some combination thereof, implemented for example in software code programmed into the processor.

The models, in turn, can be used to predict the level of oxygen saturation within the tissue being interrogated at a future point in time. As a result, the models can be used to determine the amount of time that DHCA (or other procedures) can be performed prior to the arrival of a critical $SctO_2$ threshold value (or amount of change in $SctO_2$ from a starting $SctO_2$ value at initialization of DHCA). The models therefore can provide a tool for applications such as predicting the duration of circulatory arrest that a patient can withstand safely, and one that can aid in determining how long a patient must be cooled (e.g., at 12-15° C.) to increase $SctO_2$ to the desired or highest possible value before commencing circulatory arrest.

The length of circulatory arrest that can be tolerated without neurological sequelae can vary considerably among individual subjects. As a result, techniques that use generalized time and temperature recommendations for avoiding cerebral ischemia are suboptimal for patient care. The present invention, in contrast, permits an anesthesiologist to provide a surgeon with a warning based on real-time accurate data regarding the possibility of cerebral ischemia. The ability to forewarn the surgeon regarding the amount of "safe time" left in which to complete the procedure will allow the surgeon to select alternative cerebral perfusion strategies if the repair cannot be completed within the allotted time (e.g. selective cannulation of head vessels, perfusion of the right vertebral artery and right carotid artery with collateralization via the circulus of Willis, etc.).

In some embodiments of the present invention, the above described modeling can be performed on a real-time basis, wherein the models are updated periodically thereby providing a dynamic model that adapts as necessary over time; e.g., adapts during the procedure being performed. For example, the processor can be adapted to create a current saturation model using currently determined $SctO_2$ values (e.g., in a manner described above), and that current model can then be evaluated relative to an earlier saturation model to determine what changes, if any, in the predicted saturation rate of change. Based on those determinations, the model can then be adjusted as necessary, including adjustments regarding the amount of time predicted until a threshold SctO2 value is expected.

The ability of the present invention to perform the saturation rate of change modeling in real-time provides considerable advantage. The desaturation rate for a patient is a function of several variables, which variables are held as constants in a "static" model. For example, a model embodiment that does not adjust in real-time would likely be based on certain assumptions such as the subject remaining in a supine position while undergoing deep hypothermia at 12-15° C. If more mild hypothermia is used during DHCA, a higher rate of $SctO_2$ desaturation may occur due to higher metabolism of the subject. In addition, if the subject's head is in a position other than supine, the redistribution of blood volume under the cerebral oximetry sensors may be different than the data used to create the model. Subjects with lower initial hematocrit during DHCA may experience a higher rate of $SctO_2$ desaturation due to lower hemoglobin levels of the trapped blood in the cerebral microvascular system. Also, the size or geometry of the head of the subject, such as a pediatric subject, may affect the rate the blood volume redistributes in the head during DHCA. Consequently, although a "static" model represents a considerable improvement over the present state-of-the-art, assumptions made within the static model do not need to be made in the above-described dynamic model.

The following example is provided to illustrate the operation of the present invention.

With institutional review board approval and informed consent, 30 patients undergoing elective thoracic aortic surgery with DHCA, with or without antegrade selective cerebral perfusion (SCP), were monitored intraoperatively using a FORE-SIGHT® cerebral oximeter. After the induction of general anesthesia, two sensors were placed on each subject's forehead bilaterally for continuous monitoring of $S_{ct}O_2$. The subjects remained in the supine position during surgery, allowing for only minor positional changes to facilitate surgical exposure. There was no alteration in surgical technique or routine clinical monitoring.

General anesthesia was induced in all subjects with etomidate, fentanyl and midazolam. Muscle relaxation was achieved with vecuronium prior to endotracheal intubation. A balanced anesthetic technique was employed for maintenance consisting of isoflurane (0.6-1.5 Vol %), fentanyl, vecuronium and midazolam. All subjects were mechanically ventilated with $FiO_2$ 100% in a volume controlled mode, maintaining $paCO_2$ at 35-45 mmHg.

All subjects were monitored using a left sided radial arterial catheter, a pulmonary artery catheter inserted via the right internal jugular vein, a 20 gauge jugular bulb catheter inserted via the left internal jugular vein for intermittent sampling of jugular venous blood, and a Foley bladder catheter with integrated temperature monitoring capability (Core temperature).

After insertion of the jugular bulb catheter, a baseline measurement was obtained to confirm proper placement. Serial measurements (every 10 minutes) were then acquired once on cardiopulmonary bypass (CPB) and the patient's core temperature was decreased to about 20° C. DHCA was commenced once two consecutive measurements were obtained with values greater 95% and a total cooling time of 45 minutes was exceeded. Most patients will fulfill the abovementioned criteria at core temperatures between 12-15° C.

Subjects were placed on CPB after cannulation of the right axillary artery. Venous drainage was achieved via a two-stage cannula inserted into the appendage of the right atrium. All patients received antegrade cardioplegia at 30 minute intervals. α-stat management was utilized during CPB for both cooling and warming phases.

The FORE-SIGHT® cerebral oximeter utilized in the aforesaid study, uses near-infrared spectroscopy (NIRS) techniques with interrogating light along four wavelengths in the infra-red spectrum (e.g., 690, 780, 805 and 850 nm) to determine the concentration of oxy-hemoglobin ($HbO_2$) to the concentration of deoxy-hemoglobin (Hb) primarily in the microvasculature. The cerebral tissue oxygen saturation ($S_{ct}O_2$) is determined by considering, inter alia, at the ratio of $HbO_2/(HbO_2+Hb)$. Because the blood in the cerebral microvasculature is a mix of arterioles, venuoles, and capillaries, the cerebral oximeter interrogates both venous and arterial blood with the approximate contribution ratio of venous blood volume to arterial blood volume of about 70/30%, respectively, based on Positron Emission Tomography (PET) studies and high temporal resolution sampling of internal jugular venous blood.

The FORE-SIGHT® cerebral oximeter is operable to calculate total hemoglobin concentration in a subject's tissue by the following equation: TotalHb=$HbO_2$+Hb. To avoid confusion to conventional hemoglobin concentration measurements (HGB) in blood, measured in g/dL, the FORE-SIGHT® cerebral oximeter measures hemoglobin concentration per volume of tissue (units: micromoles Hb per liter or 1000 $cm^3$ of tissue, abbreviated μM). TotalHb is usually proportional to HGB or blood hematocrit and decreases during hemodilution, a common occurrence seen in cardiac surgery as a consequence of the asanguineous prime required by the CPB circuit. Therefore, at commencement of CPB, a decline in TotalHb is typically observed. On the other hand, a rise in TotalHb can be expected at separation from CPB if autologous red blood cells are transfused or cell saver salvaged blood is returned to the patient resulting in an increase of blood hematocrit. Additionally, TotalHb is also sensitive to autoregulatory mechanisms within the vasculature. Increased blood vessel diameter in response to acidosis, potassium concentration or $CO_2$ partial pressure will result in an increased hemoglobin concentration in tissue, which will result in an increase in TotalHb. Usually, an increase in cerebral blood flow from hemodynamic changes such as increased cardiac output will increase TotalHb as well. A decrease in cerebral perfusion due to low cardiac output, DHCA, clamping of major cerebral blood vessels, or low perfusion pressure can all result in a decrease in TotalHb.

If the HGB or blood hematrocrit (Hct) is relatively constant during the measurement period, then changes in TotalHb are proportional to changes in cerebral blood volume (CBV) as can be seen from the following equation:

$$\Delta CBV \approx \Delta TotalHb * K/Hct \text{ (mL blood/100 g tissue);} \quad \text{[Eqn. 1]}$$

where the constant "K" is a conversion factor from TotalHb to CBV that includes the molecular weight of hemoglobin, tissue density, and cerebral to large vessel hematocrit ratio.

$SctO_2$ and TotalHb data determined from the FORE-SIGHT® cerebral oximeter were recorded every two seconds, along with major perioperative events from an anesthesia information management system (AIMS) (e.g., CompuRecord, Philips Medical Systems, Andover, Mass.). Each subject's left and right sensor data were averaged together for each event, and mean and standard deviation were determined For $SctO_2$ data recorded during DHCA, linear and non-linear regression techniques were utilized to characterize the decline of $SctO_2$ as a function of DHCA duration.

Figure 4:
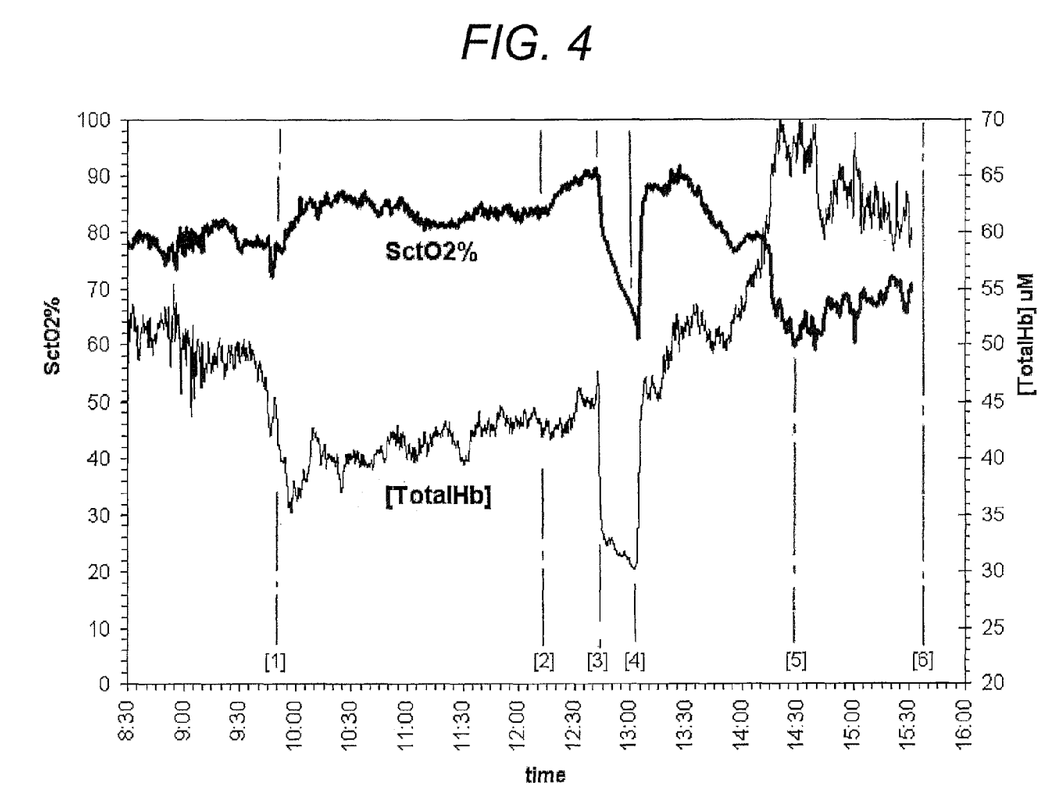
FIG. 4 is a graph depicting $SctO_2$ and TotalHb cerebral oximetry data collected from a study of 30 subjects.
Figure 5:
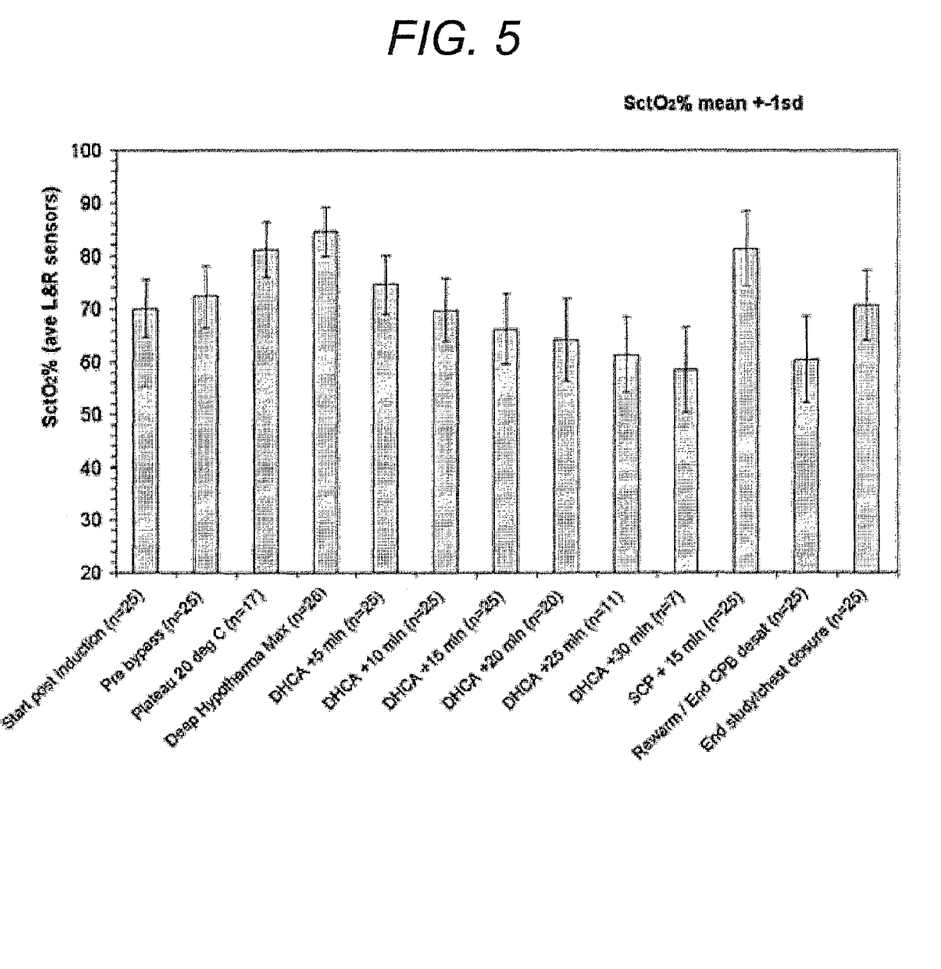
FIG. 5 illustrates $SctO_2$ mean data collected at various points, and the standard deviation thereof.

Analysis of the cerebral oximetry data showed that 26 of the 30 subjects had similar $SctO_2$ patterns as demonstrated in FIG. 4. The events noted in FIG. 4 include: [1] On CPB, cool to 20° C., and hemodilution; [2] Cool to 12° C.; [3] DHCA start; [4] DHCA end; [5] End CPB; and [6] Chest closed. The $SctO_2$ mean and standard deviation from the 26 typical subjects sorted by surgical events are shown in FIG. 5. Post induction $SctO_2$ was 70.0±5.3% (1 standard deviation). During cooling on CPB, a rise in $SctO_2$ was found in most subjects. During deep hypothermia when the subjects were cooled to 12-15° C., $SctO_2$ values increased in most subjects above 80% (84.3±4.6%, 21/30 subjects). The rate of $SctO_2$ increase tended to match the rate of core cooling. After the onset of DHCA, $SctO_2$ decreased as a function of DHCA duration (e.g., see FIG. 5). Mean $SctO_2$ decreased to 58.4±8.3% after 30 minutes of DHCA, then returned to near pre-DHCA levels 81.2±7.1% during SCP/post DHCA. During the rewarming phase and weaning off CPB, cerebral desaturation events were commonly observed, with $SctO_2$ transiently dropping to a mean of 60.4±8.3% before recovering to 70.6±6.7% at the end of the procedure.

To determine a rate of $SctO_2$ decline during DHCA, $SctO_2$ values were collected from the following events from the 26 typical cases: DHCA Onset (n=26), +5 minutes post DHCA Onset (n=25), +10 minutes (n=25), +15 minutes (n=25), +20 minutes (n=20), +25 minutes (n=11), and +30 minutes (n=7). For each category, the $SctO_2$ mean and standard deviation was determined. (See FIG. 6)

Figure 6:
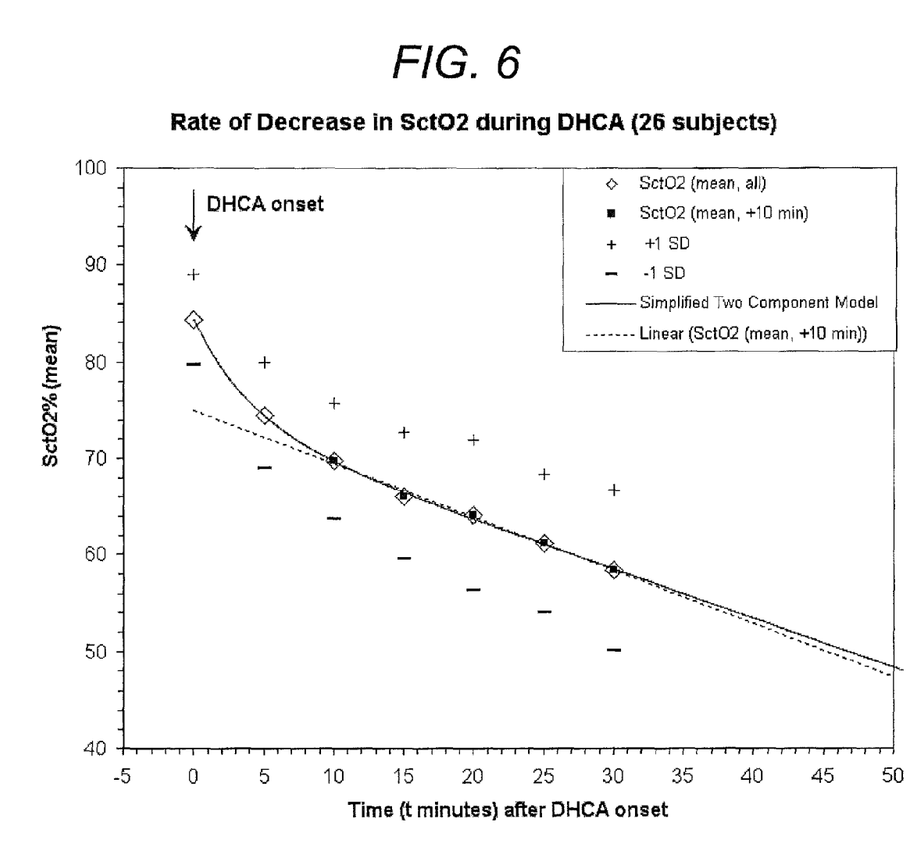
FIG. 6 illustrates models of $SctO_2$ data as a function of time.

Using non-linear regression, the $SctO_2$ data was fit to several different models; e.g., to a linear model, a simplified non-linear two-component model, and a non-linear two-component model. The present invention is not limited to these models, however.

As can be seen from FIG. 6, a two-component model fits well in view of the two distinct phases within the data; e.g., in the first ten (10) minutes of data shown in FIG. 6, the rate of change of the $SctO_2$ saturation level was greater than the subsequent rate of change, which was substantially more linear. The following is an example of an algorithmic embodiment of a simplified two-component model, where t is in minutes:

$$SctO_2(t) = 73.81 + 10.53 * \exp(-0.238 * t) - 0.51 * t \quad \text{[Eqn. 2]}$$

For trending $SctO_2$ ($SctO_2$=0 at DHCA onset) or for any $SctO_2$ value at t=0, this embodiment of the model can be rewritten as:

$$SctO_2(t) = SctO_2(t_0) - 10.53 + 10.53 * \exp(-0.238 * t) - 0.51 * t \quad \text{[Eqn. 3]}$$

An example of an algorithm for the non-linear two-component model is as follows:

$$SctO_2(t) = 1306.62 + 10.48 \cdot \exp(-0.239 \cdot t) + 1380.5 \cdot \exp(-0.000372 \cdot t) \quad [\text{Eqn. 4}]$$

In another example, the linear model was closely fitted to the data for the period of time after the first ten (10) minutes after onset of DHCA. An exemplary algorithmic embodiment of that linear model is as follows:

$$SctO_2(t) = -0.55 \cdot t + 74.95 \quad [\text{Eqn. 5}]$$

Under this model, the $SctO_2$ decreased at a mean rate of 0.55% per minute after 10 minutes. This desaturation rate compared well to the simplified two-component model, where the $-0.51 \cdot t$ term approximated the decrease in $SctO_2$ of 0.51% per minute after 10 minutes.

Figure 7:
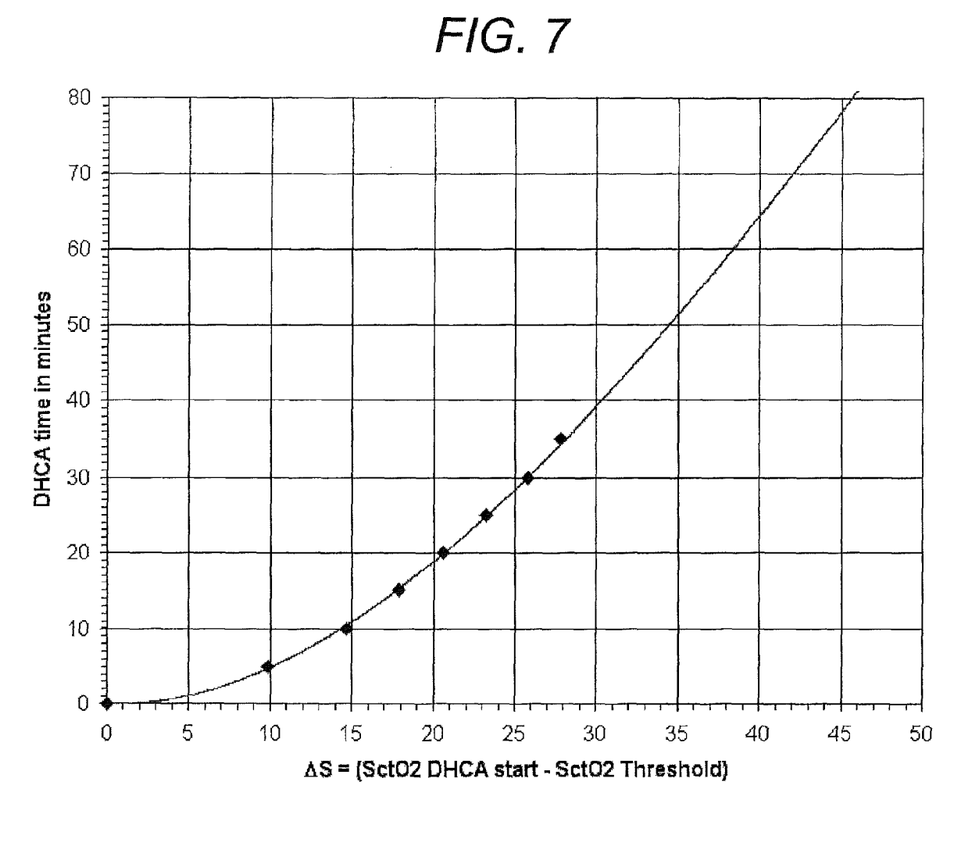
FIG. 7 illustrates safe procedure (e.g., DHCA) time as a function of the change in $SctO_2$.

Under the present invention, models such as those described above can be used to determine the amount of time that DHCA (or other procedure) can be performed prior to the arrival of a critical $SctO_2$ threshold value (or amount of change in $SctO_2$ from a starting $SctO_2$ value at initialization of DHCA). For example, the non-linear regression model provided above in Eqn. 3, can be rewritten to determine an estimated safe DHCA time "t" in minutes:

$$t = 111.69 \cdot \exp[-0.03364 \cdot \Delta S] + 3.67 \cdot \Delta S - 111.65 \quad [\text{Eqn. 6}]$$

where $\Delta S = SctO_2$ DHCA start $- SctO_2$ Threshold. FIG. 7 graphically illustrates the DHCA time in minutes versus the change in $SctO_2$ from the starting $SctO_2$ value at initialization of DHCA. The value of "t" can be determined from an equation such as that disclosed above, or alternatively the solution could be determined using a look-up table or a graphical solution (e.g., given a selected $\Delta S$ value), all of which can implemented in software code.

As indicated above, in some embodiments the processor of the present invention can be adapted to operate in a real-time mode (i.e., a "dynamic" model versus a "static model"). For example, present invention desaturation rate-of-change models can be created in real time using regression techniques from collected data:

$$\text{DHCA time } t = A \cdot \exp[K \cdot \Delta S] + B \cdot \Delta S + Z \text{ (in minutes)} \quad [\text{Eqn. 7}]$$

where $\Delta S$ is defined as provided above, and for each segment predicted, the predicted curve is evaluated relative to the model and real-time collected data to determine the variables "A", "K", "B", and "Z" from the equation above by using non-linear regression. Based on those determinations, the next predicted segments of the model are adjusted as necessary. The amount of time remaining until a predetermined minimum value, after which the oxygen saturation is too low and the flow of oxygenated blood must be resumed to the brain to avoid damage, is iteratively calculated using the model, which is updated as necessary. As a result of the real-time adaptation of the model, the amount of time left before the minimum oxygen saturation value is reached can be determined with a desirable degree of accuracy.

In an alternative embodiment which is less computational intensive, the model can be adapted by real-time modeling the rate of change of the oxygen saturation level once the desaturation rate has entered the linear phase; e.g., using the data in FIG. 6 as an example, after 10 minutes of DHCA. In such a case, a linear model for the aforesaid period could be used:

$$\text{DHCA time } t = B \cdot \Delta S + Z \text{ (in minutes)} \quad [\text{Eqn. 8}]$$

For each segment predicted using the model, the predicted linear relationship is evaluated relative to the existing model and the collected data to determine the variables "B" and "Z" using linear regression, and the next predicted segments of the model are adjusted as necessary. For example, by using real-time linear regression, two minute segments of $SctO_2$ data can be analyzed to determine "B" and "Z" of the above model above. The updated model can then be used to calculate the time remaining until the subject, who is in DHCA, will reach the SctO2 predetermined safe threshold. Alternatively, time remaining to the SctO2 threshold can be determined by a moving window of data (e.g., a two minute window), in which linear regression is used to update the model every few seconds.

While the invention has been described with reference to an exemplary embodiment and example, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A spectrophotometric examination device, comprising:
   at least one sensor having a light signal transmitter operable to transmit at least one light signal, and at least one light signal detector operable to detect the light signal, which sensor is operable to produce at least one sensed signal corresponding to the detected light signal; and
   a processor adapted to determine an oxygen saturation level in a subject's tissue at a current point in time using the sensed signal, and which processor is adapted to model a rate of change in oxygen saturation level within the subject's tissue using a non-linear multi-component model, and determine an amount of time between the current point of time and a future point of time when the oxygen saturation level will reach a predetermined value.

2. The device of claim 1, wherein the processor is adapted to model the rate of change in oxygen saturation level within the subject's tissue on a periodic basis, and update the amount of time between the current point of time and a future point of time in the event of change.

3. A method for determining cerebral oxygen saturation in a subject, comprising the steps of:
   determining tissue oxygen saturation values using a NIRS type oximeter over a period of time;
   modeling a rate of change in the tissue oxygen saturation values on a non-linear multi-component basis; and
   determining an amount of time until a predetermined tissue oxygen saturation value is reached using the modeling of the tissue oxygen saturation values.

4. The method of claim 3, wherein the step of modeling the rate of change in oxygen saturation level within the subject's tissue is performed on a periodic basis, and includes updating the amount of time until the predetermined tissue oxygen saturation value is reached.

* * * * *